(12) United States Patent
Urbizu de Cabo

(10) Patent No.: US 6,826,798 B1
(45) Date of Patent: Dec. 7, 2004

(54) TOOTHBRUSH

(76) Inventor: Ramon Pedro Urbizu de Cabo, Lautaro 885, Temuco (CL)

(*) Notice: Subject to any disclaimer, the term of this patent is extended or adjusted under 35 U.S.C. 154(b) by 0 days.

(21) Appl. No.: 10/130,807

(22) PCT Filed: Oct. 25, 2000

(86) PCT No.: PCT/AT00/00280
§ 371 (c)(1),
(2), (4) Date: May 21, 2002

(87) PCT Pub. No.: WO01/37702
PCT Pub. Date: May 31, 2001

(30) Foreign Application Priority Data

Nov. 22, 1999 (CL) .......................................... 2716-1999

(51) Int. Cl.[7] .............................. A46B 9/04; A46B 17/00
(52) U.S. Cl. ......................................... 15/167.1; 15/246
(58) Field of Search .............................. 15/110, 167.1, 15/246, 248.1

(56) References Cited

U.S. PATENT DOCUMENTS

| | | | | |
|---|---|---|---|---|
| 851,550 A | * | 4/1907 | Nevius ........................ 15/248.1 |
| 1,501,020 A | * | 7/1924 | Small ........................ 15/248.1 |
| 1,509,720 A | | 9/1924 | Donnell ........................ 15/25 |
| 2,121,358 A | * | 6/1938 | Loeffler ..................... 15/167.1 |
| 2,179,266 A | * | 11/1939 | Lukenbill .............. 15/167.1 X |
| 2,290,454 A | * | 7/1942 | Steinberg ............... 15/167.1 X |
| 2,722,703 A | * | 11/1955 | Green .................. 15/167.1 X |
| 2,835,912 A | * | 5/1958 | Pensky .................. 15/167.1 X |
| 2,845,649 A | * | 8/1958 | Hutson ..................... 15/167.1 |
| 3,968,950 A | * | 7/1976 | Gallo .................... 15/167.1 X |
| 4,259,761 A | * | 4/1981 | Earle ..................... 15/167.1 X |
| 5,735,691 A | | 4/1998 | Fetter ......................... 433/140 |
| 5,822,821 A | | 10/1998 | Sham ......................... 15/22.1 |
| 5,875,516 A | * | 3/1999 | Blue ......................... 15/248.1 |

FOREIGN PATENT DOCUMENTS

| | | | | |
|---|---|---|---|---|
| FR | 750214 | * | 8/1933 | ............... 15/248.1 |
| FR | 910868 | | 2/1946 | |
| FR | 2310723 | * | 12/1976 | ............... 15/248.1 |
| FR | 2380751 | * | 9/1978 | ............... 15/248.1 |

* cited by examiner

*Primary Examiner*—Mark Spisich
(74) *Attorney, Agent, or Firm*—Collard & Roe, P.C.

(57) ABSTRACT

A toothbrush has a handle (4) and a possibly electrically drivable brush head (2), which is connected to the handle (4) via a neck part (5). In order to provide advantageous construction conditions, a guide (6), which encloses the neck part (5) with movement play, forms a bite support.

9 Claims, 3 Drawing Sheets

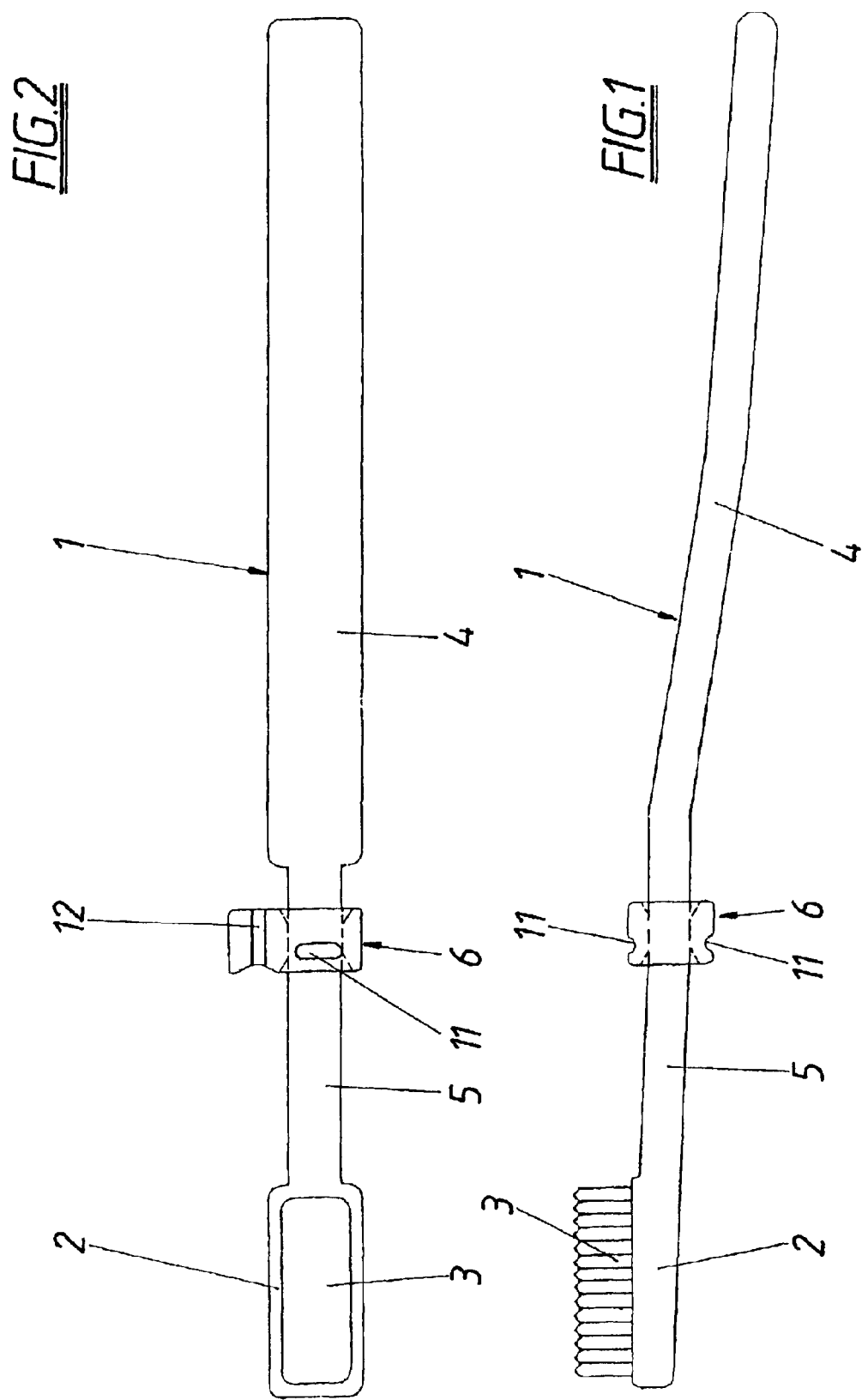

TOOTHBRUSH

CROSS REFERENCE TO RELATED APPLICATIONS

Applicant claims priority under 35 U.S.C. §119 of Chilean Application No. 2716-99 filed on 22 Nov. 1999. Applicant also claims priority under 35 U.S.C. 365 of PCT/AT00/00280 filed on 25 Oct. 2000. The international application under PCT article 21(2) was not published in English.

BACKGROUND INFORMATION

The present invention relates to a toothbrush having a handle and a possibly electrically drivable brush head, which is connected to the handle via a neck part.

The success of toothbrushing, particularly of the molars, depends above all on exact guiding of the brush head along the inside and outside of the molars, the brush bristles to be guided from the gums to the crown of the tooth while the brush head simultaneously rotates halfway around the axis of the neck part. These brushing movements, which are to be performed by hand even with electrically driven brush heads, are difficult because there are no support points for the hand or for the toothbrush, so that the brush head frequently slides off and toothbrushing is strenuous and incorrect. It must be considered in this connection that for correct guiding of a typical toothbrush, the elbow has to be raised, which is tiring and, in addition, is a reason that the rotational movement of the toothbrush which is advantageous for guiding the brush head along the molars is not performed with the required precision while sufficient pressure is applied. This is true above all for the inside of the molars, because on the outside of the molars the brush head does find support on the inside of the cheek for guiding the toothbrush, but not on the inside of the molars. The special curves of the neck part of known toothbrushes produces just as few advantages in this connection as special bristle arrangements, because it primarily depends on maintaining exact brushing movements along the molars, which therefore depend on the skill and attentiveness of the brusher.

DESCRIPTION OF THE INVENTION

The present invention therefore has the object of designing a toothbrush of the type initially described in such a way that the brusher experiences effective support during proper handling of the toothbrush, so that good brushing success may be achieved without special skill and attentiveness.

This object is achieved by the present invention by a guide, surrounding the neck part with movement play, which forms a bite support.

The guide for the toothbrush, which surrounds the neck part of the toothbrush with movement play, offers, in a simple way, the advantageous possibility of supporting the toothbrush near the respective tooth to be brushed in such a way that not only is exact guiding of the brush head along the inside and outside of the molars made significantly easier, but the necessary pressure may also be exercised on the tooth surfaces to be cleaned without a tiring application of force, because advantageous lever ratios for the handling of the toothbrush are ensured by the support of the neck part on the guide. However, this requires that the guide for the neck part of the toothbrush may itself be fixed without movement in relation to the teeth to be cleaned. This is easily achieved in that the guide forms a bite support, i.e., is held tightly between the teeth. By dislocating this bite support between the teeth, a course of the neck part of the toothbrush in the guide which is more favorable for cleaning the individual teeth may always be achieved.

If the guide itself is taken between the teeth as a bite support, passing the toothbrush between the rows of teeth through the guide to the inside of the molars is simple. Taking the guide between the teeth in this way makes brushing the outside of the molars difficult, however, if a guide body which has a basically cylindrical shape is assumed. In order to also achieve guide conditions which are advantageous for brushing the outside of the molars, the guide may have a holding projection directed away from the neck part, which is used as a bite support for brushing the outside of the teeth, so that the guide comes to rest outside the rows of teeth.

Although the guide for the neck part of the toothbrush may be implemented in different ways, particularly simple construction relationships result if the guide forms a pass-through opening for the neck part, so that the neck part finds the necessary support for operation of the toothbrush in the correct position in the pass-through opening which encloses it. In this case, the guide generally forms an annular main body, the axial guide length of the pass-through opening to be smaller than the length of the neck part, so that the neck part may be moved back and forth axially inside the pass-through opening. The rotational movement of the toothbrush around the axis of the neck part and/or the pass-through opening results on its own. If the brush head of the toothbrush is additionally to be pivoted around a transverse axis, then an appropriate pivot angle may be easily ensured if the pass-through opening of the guide expands conically toward both the brush head and the handle.

For better holding of the guide between the upper and lower rows of teeth, it may be provided with at least one bite recess, which is preferably tailored to the typical course of the teeth and offers a good hold for the teeth. For a holder of the guide in the region of the pass-through opening, the bite recesses advantageously run transverse to the neck part, because in this case the toothbrush must be guided between the upper and lower rows of teeth toward the inside of the molars. For brushing the outside of the molars, a toothbrush guide aligned essentially in the direction of the rows of teeth is to be ensured, so a bite recess on the holding projection in the direction of the axis of the neck part is advantageous.

If the pass-through opening of the guide is implemented as closed on its circumference, the guide will be held captively on the neck part of the toothbrush. In order to be able to retrofit a typical toothbrush using a guide according to the present invention or to provide the possibility of removing this guide from the toothbrush, the guide may form a pass-through opening for the neck part which is open on its circumference and which may be placed on the neck part by elastically expanding the pass-through opening transverse to the neck part.

BRIEF DESCRIPTION OF THE DRAWING

The object of the present invention is illustrated for exemplary purposes in the drawing.

FIG. 1 shows a toothbrush according to the present invention in a schematic side view, FIG. 2 shows this toothbrush in a horizontal projection.

DETAILED DESCRIPTION OF THE EMBODIMENTS

Figure 3:
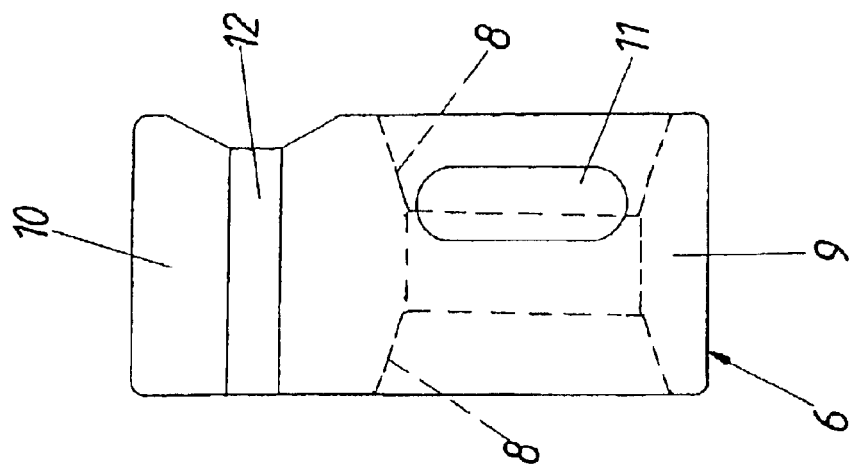
FIG. 3 shows the guide for the neck part of the toothbrush shown in FIGS. 1 and 2 in a horizontal projection in a larger scale.
Figure 4:
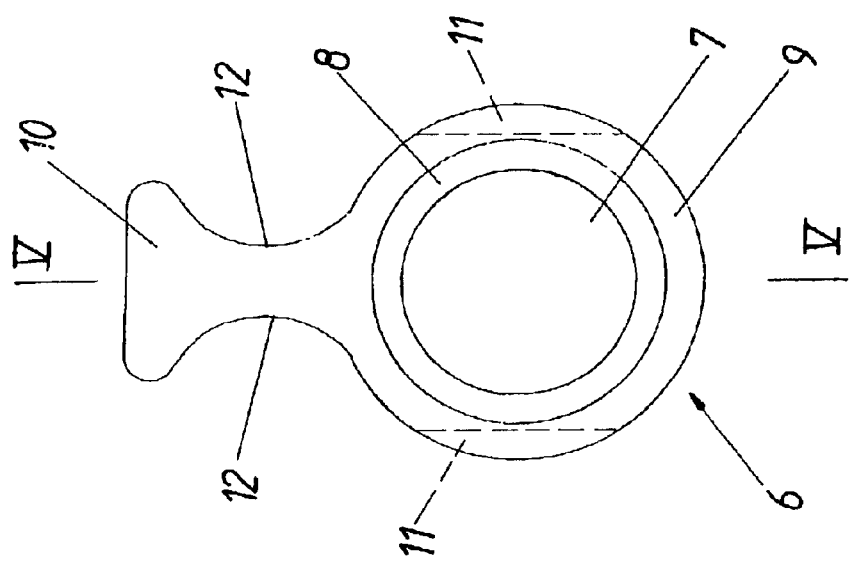
FIG. 4 shows this guide in an end view.
Figure 5:
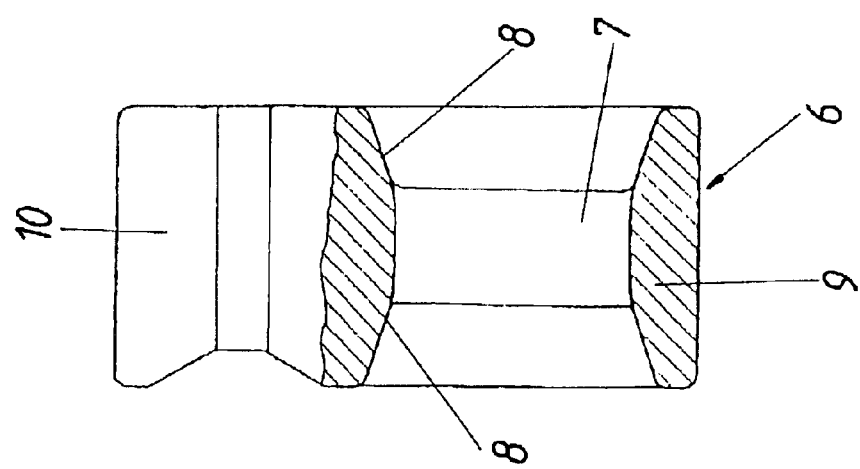
FIG. 5 shows a section along the line V—V of FIG. 4.
Figure 7:
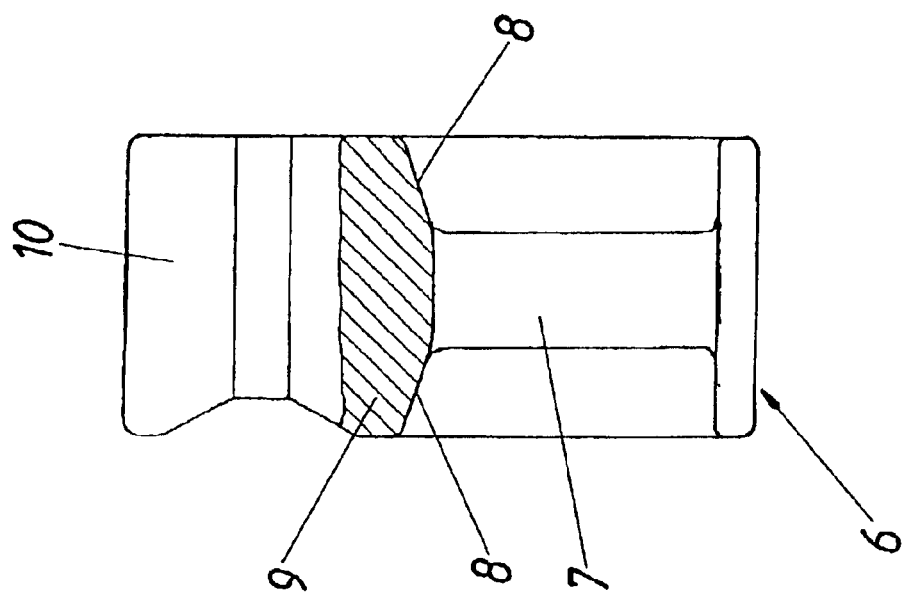
FIG. 7 shows a section along the line VII—VII of FIG. 6.
Figure 6:
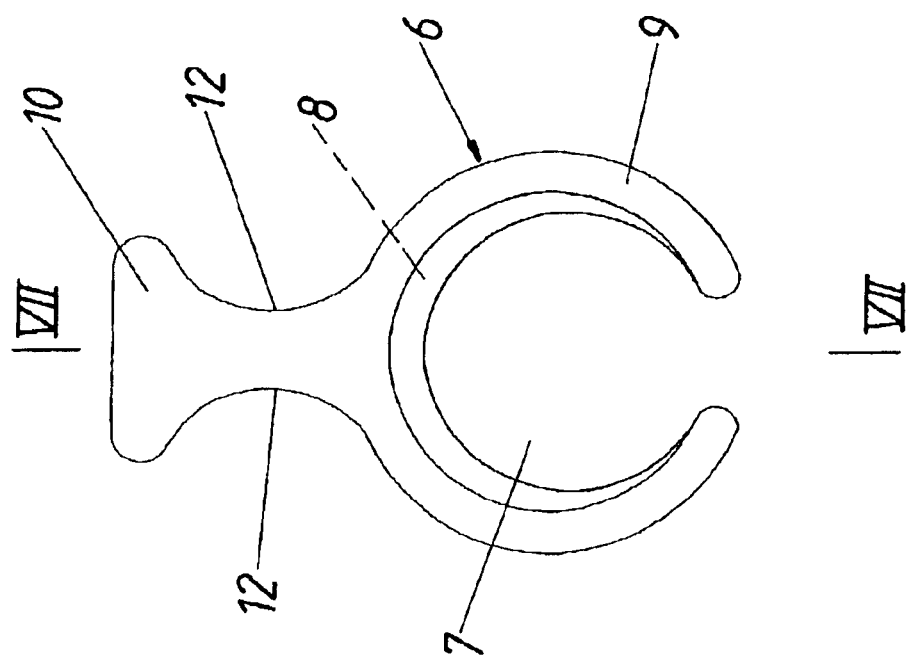
FIG. 6 shows an illustration of a construction variation of a guide corresponding to FIG. 4.

The toothbrush schematically illustrated in FIGS. 1 and 2 has a shaft 1 having a brush head 2 located on the forward shaft end whose bristles are indicated with 3. Shaft 1 is divided into a handle 4 and a neck part 5 offset from both brush head 2 and handle 4. In contrast to typical toothbrushes of this type, a guide 6, which encloses neck part 5 with movement play, is provided, which forms a bite support so that guide 6 may be held between the upper and lower rows of teeth. Guide 6 has a pass-through opening 7 for neck part 5, which is closed on its circumference as shown in FIGS. 3 to 5, but may also be implemented as open on the circumference, corresponding to the embodiment shown in FIGS. 6 and 7. In both embodiments, pass-through opening 7 forms a cylindrical central part from which conical expansions 8 extend toward both sides. Since the guide length of pass-through opening 7 is smaller than the axial length of neck part 5, neck part 5 of the toothbrush may be axially displaced inside pass-through opening 7. In addition, a rotational movement of neck part 5, which is additionally held pivotably and delimited on all sides in guide 6 due to conical expansions 8, around the axis of pass-through opening 7 is possible. If guide 6 is now held tightly between the upper and lower rows of teeth as a bite support in the region of the front teeth, the toothbrush may only be guided by hand in the movement region given by guide 6, which, due to the toothbrush support directly next to the brushing region, allows not only exact placement of the brush head on the tooth to be brushed, but also the maintenance of advantageous brushing movements of brush head 2.

If annular main body 9 of guide 6 is held tightly between the front teeth, pass-through opening 7 leads to the inside of the upper and lower rows of teeth, which significantly simplifies the brushing of the inside of the molars. Such a position of guide 6 is, however, not suitable for brushing the outside of the molars. For this reason, annular main body 9 is provided with a holding projection 10 directed away from neck part 5, which also represents a bite support and allows guide 6 to run, outside the rows of teeth, in the direction of the rows of teeth, which is an advantageous requirement for brushing the outside of the molars. Holding guide 6 between the teeth may be made easier by bite recesses 11 and 12, which, due to their alignment, predetermine the most favorable position of the guide between the teeth at any time. For this purpose, bite recesses 11 may, for example, run transverse to neck part 5 in the region of main body 9 forming pass-through opening 7. Bite recesses 12 on holding projection 10 are, however, aligned in the direction of neck part 5 in order to be able to perform the brushing of the outside of the molars with an appropriately guided toothbrush.

As FIGS. 1 and 2 show, guide 6 may be positioned captively on neck part 5 of the toothbrush, particularly if pass-through opening 7 is implemented as closed on its circumference, corresponding to the embodiment shown in FIGS. 3 to 5. However, pass-through opening 7 for neck part 5 of the toothbrush is open on the circumference according to FIGS. 6 and 7, so that guide 6 may be placed on neck part 5 transverse to neck part 5, by elastically expanding pass-through opening 7. Such an embodiment of guide 6 allows simple retrofitting of typical toothbrushes with guide 6 according to the present invention.

The present invention is, of course, not restricted to the exemplary embodiments illustrated. Therefore, the toothbrushes may have different shaft shapes and bristle arrangements or may be provided with electrically driven brush heads, because it merely concerns the support of the handling of the toothbrush by a guide which may be held firmly between the teeth, which supports movements of the brush head advantageous for the handling of the toothbrush.

What is claimed is:

1. A toothbrush for brushing the teeth forming a bite of a user, comprising
   (a) a handle,
   (b) a brush head,
   (c) a neck part connecting the brush head to the handle, the neck part having a diameter smaller than the diameters of the handle and the brush part, and
   (d) a guide at least partially enclosing the neck part, the guide
      (1) having a pass-through opening holding the neck part axially movable with play, rotatable about its axis and pivotal in the pass-through opening of the guide, and
      (2) forming a bite support capable of being held tightly between the teeth during brushing.

2. The toothbrush of claim 1, wherein the guide comprises an outwardly directed holding projection.

3. The toothbrush of claim 1, wherein the pass-through opening is open on its circumference and is placeable on the neck part by elastically expanding the pass-through opening transversely to the neck part.

4. The toothbrush of claim 1, wherein the pass-through opening has an axial guide length shorter than the length of the neck part.

5. The toothbrush of claim 1, wherein the guide has at least one recess for receiving the teeth of the bite.

6. The toothbrush of claim 5, wherein the at least one recess extends transversely to the neck part.

7. The toothbrush of claim 5, wherein the guide comprises an outwardly directed holding projection, and the at least one recess extends on the holding projection lenghtwise of the neck part.

8. The toothbrush of claim 1, wherein the guide completely encloses the neck part.

9. A toothbrush for brushing the teeth forming a bite of a user, comprising
   (a) a handle,
   (b) a brush head,
   (c) a neck part connecting the brush head to the handle, the neck part having a diameter smaller than the diameters of the handle and the brush part, and
   (d) a guide at least partially enclosing the neck part, the guide
      (1) having a pass-through opening holding the neck part being freely axially movable with play, rotatable about its axis and pivotal in the pass through opening of the guide, the pass through opening expanding conically toward the handle and the brush head, and
      (2) forming a bite support capable of being held tightly between the teeth during brushing.

* * * * *